United States Patent
Billingsley et al.

(10) Patent No.: US 11,160,687 B2
(45) Date of Patent: Nov. 2, 2021

(54) VISION-PROTECTIVE HEADGEAR WITH AUTOMATIC DARKENING FILTER COMPRISING AN ARRAY OF SWITCHABLE SHUTTERS

(71) Applicant: 3M INNOVATIVE PROPERTIES COMPANY, St. Paul, MN (US)

(72) Inventors: Britton G. Billingsley, St. Paul, MN (US); Kenneth Jarefors, Borlange (SE); Kristina M. Magnusson, Djurmo (SE)

(73) Assignee: 3M Innovative Properties Company, St. Paul, MN (US)

( * ) Notice: Subject to any disclaimer, the term of this patent is extended or adjusted under 35 U.S.C. 154(b) by 56 days.

(21) Appl. No.: 16/622,607

(22) PCT Filed: Jun. 13, 2018

(86) PCT No.: PCT/IB2018/054331
§ 371 (c)(1),
(2) Date: Dec. 13, 2019

(87) PCT Pub. No.: WO2018/229688
PCT Pub. Date: Dec. 20, 2018

(65) Prior Publication Data
US 2021/0145644 A1 May 20, 2021

Related U.S. Application Data

(60) Provisional application No. 62/520,010, filed on Jun. 15, 2017.

(51) Int. Cl.
*A61F 9/06* (2006.01)
*G02F 1/1335* (2006.01)
(Continued)

(52) U.S. Cl.
CPC .............. *A61F 9/062* (2013.01); *A61F 9/065* (2013.01); *G02F 1/1396* (2013.01);
(Continued)

(58) Field of Classification Search
CPC .... A61F 9/062; A61F 9/065; G02F 1/133531; G02F 1/13312; G02F 1/13336; G02F 1/1396; G02F 1/13394; G06F 3/013
(Continued)

(56) References Cited

U.S. PATENT DOCUMENTS

| 4,848,890 A | 7/1989 | Horn |
| 4,968,127 A | 11/1990 | Russell |

(Continued)

FOREIGN PATENT DOCUMENTS

| WO | WO 2014/079574 | 5/2014 |
| WO | WO 2015-181340 | 12/2015 |

(Continued)

OTHER PUBLICATIONS

International Search report for PCT International Application No. PCT/IB2018/054331 dated Oct. 1, 2018, 4 pages.

*Primary Examiner* — Charles S Chang
(74) *Attorney, Agent, or Firm* — Kenneth B. Wood

(57) ABSTRACT

Protective headgear including an automatic darkening filter with an array of switchable shutters, and including a shutter control system, at least one workview image acquisition device, and at least one eye position monitoring device, wherein the shutter control system is controllably connected to each switchable shutter of the array of switchable shutters so as to control the switching of each of the switchable shutters, and is receivably connected to the at least one workview image acquisition device and to the at least one eye position monitoring device.

23 Claims, 6 Drawing Sheets

(51) Int. Cl.
   *G02F 1/133*    (2006.01)
   *G02F 1/1333*   (2006.01)
   *G02F 1/139*    (2006.01)
   *G06F 3/01*     (2006.01)
   *G02F 1/1339*   (2006.01)

(52) U.S. Cl.
   CPC ...... *G02F 1/13312* (2021.01); *G02F 1/13336* (2013.01); *G02F 1/133531* (2021.01); *G06F 3/013* (2013.01); *G02F 1/13394* (2013.01)

(58) Field of Classification Search
   USPC ..................................................... 349/13–14
   See application file for complete search history.

(56) References Cited

U.S. PATENT DOCUMENTS

| | | | |
|---|---|---|---|
| 5,015,086 A | 5/1991 | Okaue | |
| 5,076,669 A | 12/1991 | Black | |
| 5,114,218 A | 5/1992 | Black | |
| 5,184,156 A | 2/1993 | Black | |
| 5,276,539 A | 1/1994 | Humphrey | |
| 5,298,732 A | 3/1994 | Chen | |
| 5,305,012 A | 4/1994 | Faris | |
| 5,382,986 A | 1/1995 | Black | |
| 5,608,567 A | 3/1997 | Grupp | |
| 5,671,035 A | 9/1997 | Barnes | |
| 5,825,441 A | 10/1998 | Hornell | |
| 5,841,507 A | 11/1998 | Barnes | |
| 5,959,705 A | 9/1999 | Fergason | |
| 6,097,451 A | 8/2000 | Palmer | |
| 6,169,526 B1 | 1/2001 | Simpson | |
| 6,170,947 B1 | 1/2001 | Colles | |
| 6,760,080 B1 | 7/2004 | Moddel | |
| 6,786,610 B2 | 9/2004 | Faris | |
| 6,864,473 B2 | 3/2005 | Chretien | |
| 6,992,731 B1 | 1/2006 | Morris | |
| 7,008,055 B2 | 3/2006 | McLear | |
| 7,585,068 B2 | 9/2009 | Mullin | |
| 7,874,666 B2 | 1/2011 | Xu | |
| 7,884,888 B2 | 2/2011 | Magnusson | |
| 7,970,172 B1 | 6/2011 | Hendrickson | |
| 8,081,262 B1 | 12/2011 | Perez | |
| 8,143,563 B2 | 3/2012 | Broude | |
| 8,177,357 B2 | 5/2012 | Kamiya | |
| 8,791,990 B2 | 7/2014 | Luber | |
| 8,797,236 B2 | 8/2014 | Seo | |
| 9,057,944 B2 | 6/2015 | Sugiyama | |
| 9,405,135 B2 | 8/2016 | Sweis | |
| 2002/0007185 A1 | 1/2002 | Aghion | |
| 2006/0098153 A1 | 5/2006 | Slikkerveer | |
| 2011/0075092 A1 | 3/2011 | Nordyke | |
| 2011/0310318 A1 | 12/2011 | Kawagoe | |
| 2012/0127382 A1 | 5/2012 | Hirakata | |
| 2012/0224260 A1 | 9/2012 | Healy | |
| 2012/0262451 A1 | 10/2012 | Kotani | |
| 2012/0292488 A1 | 11/2012 | Saadat | |
| 2013/0194244 A1 | 8/2013 | Tamir | |
| 2013/0235286 A1 | 9/2013 | Hung | |
| 2014/0013479 A1 | 1/2014 | Magnusson | |
| 2014/0101812 A1 | 4/2014 | Richards | |
| 2014/0168546 A1* | 6/2014 | Magnusson | G02F 1/1333 349/14 |
| 2016/0175964 A1 | 6/2016 | Penoyer | |
| 2016/0262467 A1 | 9/2016 | Magnusson | |
| 2016/0267806 A1 | 9/2016 | Hsu | |
| 2018/0113508 A1* | 4/2018 | Berkner-Cieslicki | G06T 7/292 |

FOREIGN PATENT DOCUMENTS

| | | |
|---|---|---|
| WO | WO 2016-126587 | 8/2016 |
| WO | WO 2017-192421 | 11/2017 |

* cited by examiner

VISION-PROTECTIVE HEADGEAR WITH AUTOMATIC DARKENING FILTER COMPRISING AN ARRAY OF SWITCHABLE SHUTTERS

CROSS REFERENCE TO RELATED APPLICATIONS

This application is a national stage filing under 35 U.S.C. 371 of PCT/IB2018/054331, filed Jun. 13, 2018, which claims the benefit of provisional Application No. 62/520,010, filed Jun. 15, 2017, the disclosure of which is incorporated by reference in its/their entirety herein.

BACKGROUND

Automatic darkening filters are often provided on protective headgear where protection from high intensity light is desired.

SUMMARY

In broad summary, herein is disclosed a vision-protective headgear comprising an automatic darkening filter with an array of switchable shutters, and further comprising a shutter control system, at least one workview image acquisition device, and at least one eye position monitoring device. These and other aspects will be apparent from the detailed description below. In no event, however, should this broad summary be construed to limit the claimable subject matter, whether such subject matter is presented in claims in the application as initially filed or in claims that are amended or otherwise presented in prosecution.

Figure 1:
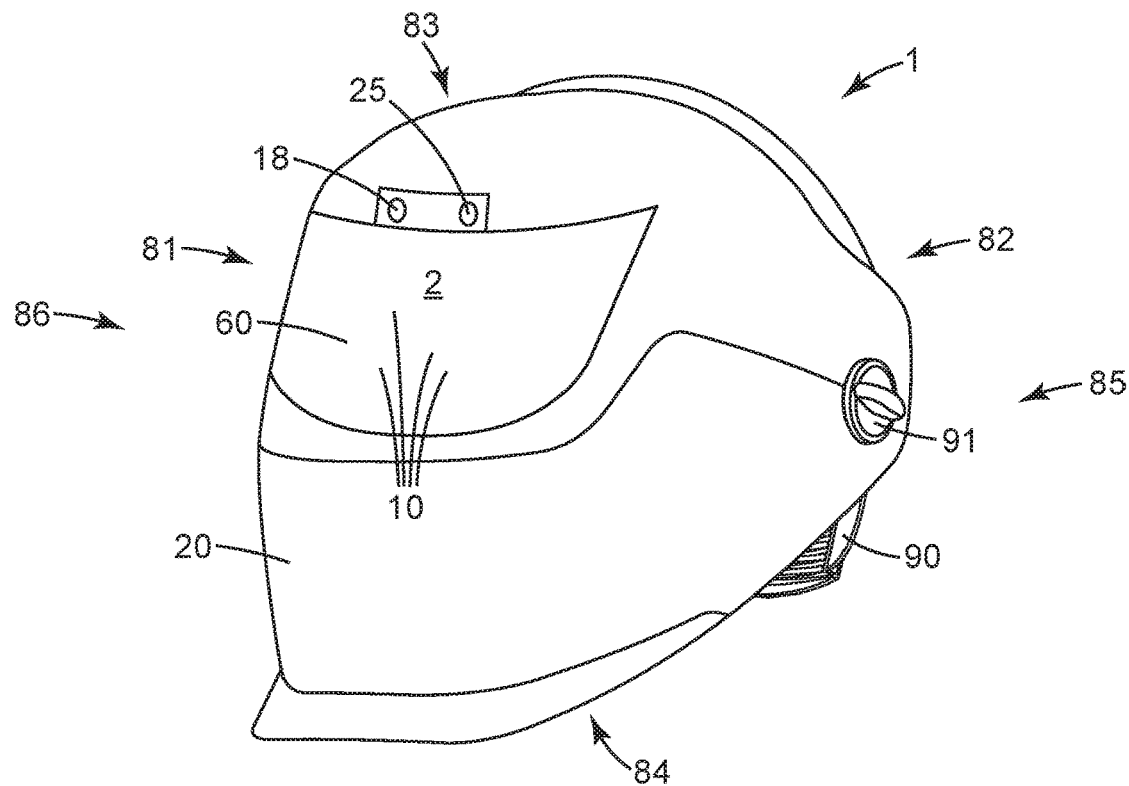
FIG. 1 is a front-side perspective view of an exemplary vision-protective headgear comprising an exemplary automatic darkening filter mounted therein.

Like reference numbers in the various figures indicate like elements. Some elements may be present in identical or equivalent multiples; in such cases only one or more representative elements may be designated by a reference number but it will be understood that such reference numbers apply to all such identical elements. Unless otherwise indicated, all figures and drawings in this document are not to scale and are chosen for the purpose of illustrating different embodiments of the invention. In particular the dimensions of the various components are depicted in illustrative terms only, and no relationship between the dimensions of the various components should be inferred from the drawings, unless so indicated. Although terms such as "top", bottom", "upper", lower", "under", "over", "front", "back", "outward", "inward", "up" and "down", and "first" and "second" may be used in this disclosure, it should be understood that those terms are used in their relative sense only unless otherwise noted. As used herein as a modifier to a property or attribute, the term "generally", unless otherwise specifically defined, means that the property or attribute would be readily recognizable by a person of ordinary skill but without requiring a high degree of approximation (e.g., within +/−20% for quantifiable properties). The term "substantially", unless otherwise specifically defined, means to a high degree of approximation (e.g., within +/−5% for quantifiable properties).

DETAILED DESCRIPTION

Herein is disclosed a protective headgear 1 comprising an automatic darkening filter 60. In various exemplary embodiments, protective headgear 1 may comprise e.g. a helmet, a shield, or a visor (e.g., a welding helmet, shield or visor), noting that there may not always be bright-line boundaries between protective headgear of these categories. As shown in exemplary embodiment in the front-side and rear-side perspective views of FIGS. 1 and 2, exemplary protective headgear 1 comprises a main body 20 that (with headgear 1 as conventionally worn by a person) comprises a generally forward side 81, a generally rearward side 82, a generally upward or top side 83 (e.g., toward the crown of a wearer's head), and a generally bottom side 84 (e.g., toward the user's neck). Main body 20 further comprises a left side 85 (denoted from the point of view of a user wearing the headgear) and a right side 86. Main body 20 comprises a generally forward-facing portion that comprises an optically-transmissive window 2. In some embodiments, optically-transmissive window 2 may take the form of a through-opening; in other embodiments, it may have one or more transparent panes mounted therein.

Figure 2:
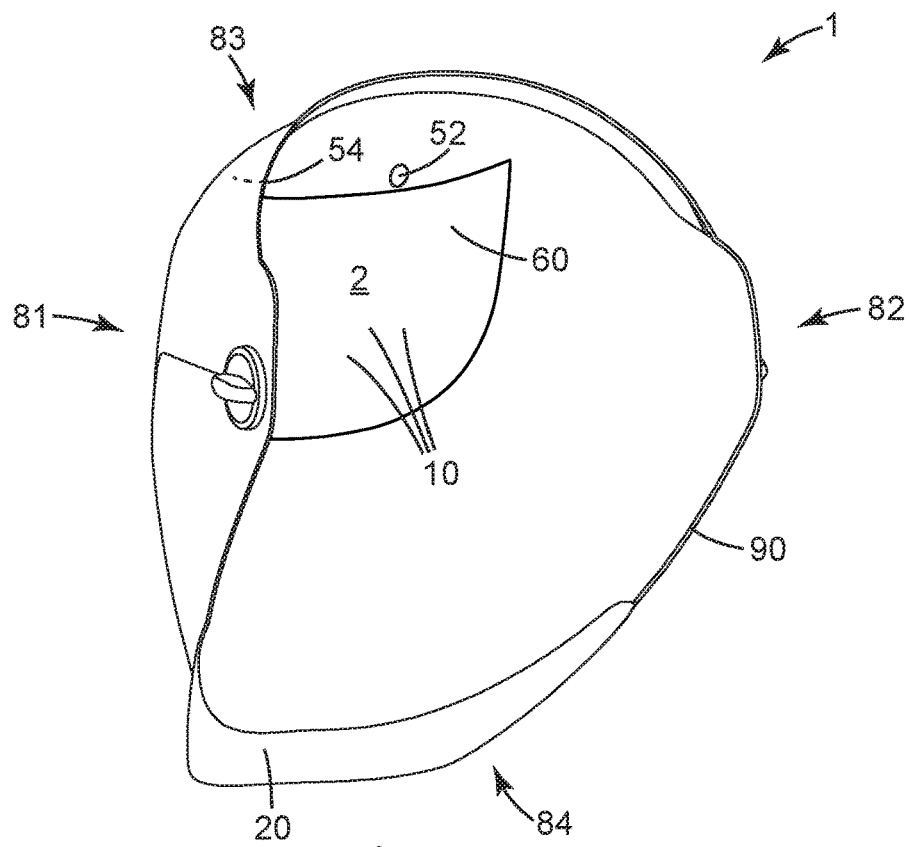
FIG. 2 is a rear-side perspective view of the exemplary protective headgear and automatic darkening filter of FIG. 1.

In some embodiments, protective headgear 1 may comprise a suspension 90, a portion of which is visible in FIG. 1 (a suspension is omitted from FIG. 2 for ease of presentation of other components of the headgear). Suspension 90 may be attached to protective headgear 1 by any suitable attachment mechanism 91. Any suspension of any suitable design may be used, and may comprise any suitable combination of e.g. brow bands, crown bands, occipital bands, and so on. In addition to such a suspension, one or more pads may be provided e.g. on the underside of the crown portion of headgear 1, which pads may serve a protective and/or cushioning function. Automatic darkening filter 60 may be mounted in protective headgear 1 (removably or permanently) in any suitable manner. In whatever manner, automatic darkening filter 60 is mounted in headgear 1 so that filter 60 is aligned with at least a portion of window 2 so that filter 60 can filter electromagnetic radiation (e.g., visible light, ultraviolet radiation, infrared radiation, etc.) that passes through window 2. That is, automatic darkening filter 60 is positioned within protective headgear 1 so that any electromagnetic radiation that reaches the eyes of a person wearing the headgear must first pass through filter 60 to be optically filtered as described herein.

In at least some embodiments, automatic darkening filter 60 is at least somewhat curved as described in detail later herein. Often, protective headgear 1 may be configured so that when the protective headgear is worn by a user, a laterally central area of filter 60 is positioned in front of the user's eyes. In some embodiments, filter 60 may comprise areas (that are integrally connected to, and extend from, the laterally central area) that wrap at least partially around toward the left and right lateral sides of the protective headgear to a desired extent. While a relatively small extent of side-wrap is present in the exemplary design of FIG. 1, any amount of side-wrap can be used as desired. If desired, filter 60 may be conveniently located rearward of one or more transparent panes, cover plates, or the like, e.g. in order to protect filter 60 from damage or debris.

Figure 3:
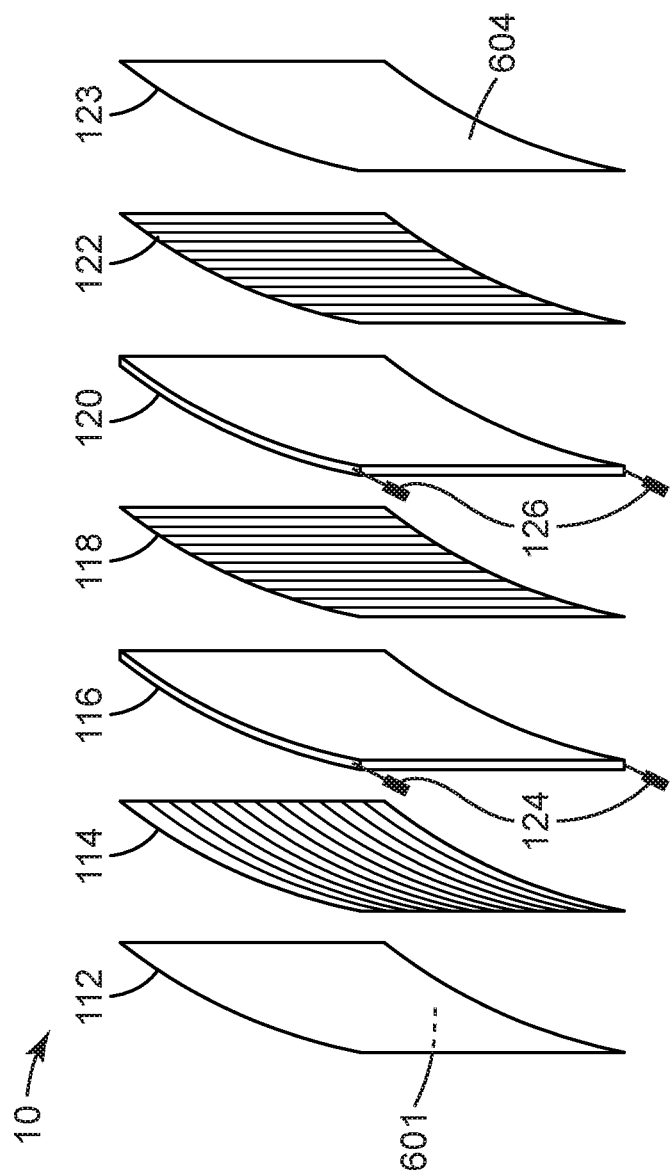
FIG. 3 is an exploded isolated side perspective view of components of an exemplary switchable shutter of a curved automatic darkening filter.

FIG. 3 shows an exploded view of an exemplary switchable shutter 10 of an exemplary curved automatic darkening filter 60. In some embodiments, one (e.g., passive) component of the shutter 110 may be a band pass filter 112 that serves to attenuate infra-red (IR) and ultra-violet (UV) wavelength components from high-intensity incident light. In some embodiments, such a band pass filter may comprise a flexible sheet upon which various layers may be deposited to form an interference filter that reflects the IR radiation and absorbs the UV-A, -B and/or -C components of the incident light. In some embodiments such a sheet may serve as a flexible front cover sheet 601 for shutter 10. In some embodiments shutter 10 may comprise a separate flexible front cover sheet that is positioned in front of a band pass filter 112. (In some embodiments, shutter 10 may comprise a flexible rear cover sheet 604 as shown in FIG. 2.)

The exemplary switchable shutter 10 as depicted in FIG. 3 includes a first polarization filter 114, a first optically-rotating liquid-crystal cell 116, and a second polarization filter 118. The first cell 116 may be a twisted, nematic, liquid-crystal cell located (sandwiched) between the first and second polarization filters 114 and 118. The polarization filters 114 and 118 have substantially orthogonal polarization directions, in which the polarization direction of the first polarization filter 114 is oriented at approximately 90° to the polarization direction of the second polarization filter 118. These orthogonal polarization directions enable cell 116 to switch to a light state, and to maintain a light state, when no control voltage is applied to cell 116; and, to switch to a dark state and to maintain a dark state when voltage is applied to cell 116 (that is, to be power-darkening), as will be well understood by the ordinary artisan.

The exemplary liquid-crystal cell of FIG. 3 also comprises a second optically-rotating liquid-crystal cell 120, located between the above-mentioned second polarization filter 118 and a third polarization filter 122. Second cell 120 may also be a twisted, nematic, liquid-crystal cell. In the illustrated embodiment, polarization filter 122 has a polarization direction that is substantially parallel to that of polarization filter 118. These parallel polarization directions enable cell 120 to switch to a dark state, and to maintain a dark state, when no control voltage is applied to cell 120; and, to switch to a light state and to maintain a light state when voltage is applied to cell 120. (This type of liquid crystal cell would be understood by the ordinary artisan to be power-lightening.)

FIG. 3 is thus representative of a general arrangement in which two liquid crystal cells 116 and 120 are interspersed among a sequence of three polarization filters 114, 118 and 122. In the particular design depicted in FIG. 3, the three polarization filters are arranged such that a first pair of polarization filters (114 and 118) are oriented substantially orthogonally to each other, and a second pair of polarization filters (118 and 122) are oriented substantially parallel to each other. Such an arrangement (in particular the presence of a pair of polarization filters that are oriented parallel to each other) may provide that one liquid-crystal cell (cell 120, in the depicted design) is a power-lightening cell, to provide an optional feature in which shutter 10 will transition to a darker state e.g. in the event of a power interruption. In other embodiments, two liquid crystal cells may be interspersed among a sequence of three polarization filters, with the polarization filters being arranged such that a first pair of the filters, and a second pair of the filters, are oriented substantially orthogonally to each other (as in the exemplary arrangement discussed later herein with reference to FIG. 6). Such an arrangement may provide enhanced angular uniformity in a dark state, particularly in the event that the shutter is desired to provide multiple dark states.

Each of the liquid-crystal cells 116 and 120 are provided with connectors 124 and 126, respectively, by which control voltages can be applied to these cells. The application of a voltage to the connectors creates an electric field between the layers of the liquid-crystal cell. The nematic, liquid-crystal molecules align with the electric field perpendicular to the defining surfaces that enclose the major sides of the cell. In a liquid crystal cell that is positioned between orthogonal polarizing filters (e.g. filters 114 and 118 of FIG. 3) this alignment of the liquid-crystal molecules, as promoted by the electric field, achieves a darkened state. In a liquid crystal cell that is positioned between parallel polarizing filters (e.g. filters 118 and 122 of FIG. 3), the opposite occurs. The degree of rotation of the liquid-crystal molecules may be controlled by varying the control voltage, and thus the corresponding filter effect also may be controlled. Thus, in some embodiments a shutter may be able to switch to, and maintain, one or more intermediate states rather than being limited to a dark state and a light state.

Figure 4:
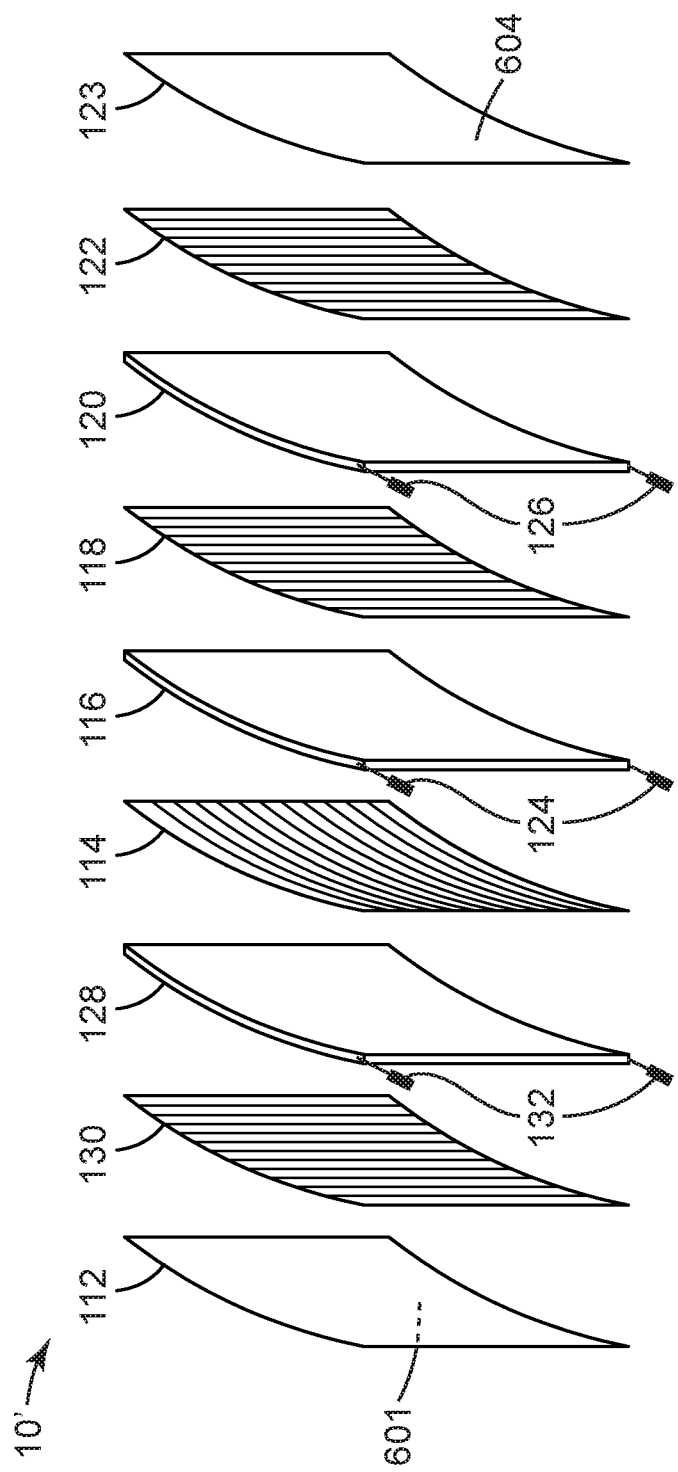
FIG. 4 is an exploded isolated side perspective view of components of another exemplary switchable shutter of a curved automatic darkening filter.

FIG. 4 shows an exploded view of a switchable shutter 110' in an alternative embodiment. Shutter 110' comprises three liquid-crystal cells 116, 120, and 128. A first liquid-crystal cell 116 is disposed between first and second polarization filters 114 and 118, a second liquid-crystal cell 120 is disposed between second and third polarization filters 118 and 122, and a third liquid-crystal cell 128 is disposed between a fourth polarization filter 130 and first polarization filter 114. In the exemplary arrangement of FIG. 3, first and third liquid-crystal cells 116 and 128 are each sandwiched between pairs of polarization filters that are oriented at least substantially orthogonally to each other, so that liquid-crystal cells 116 and 128 are of the power-darkening type of cell referred to above. Liquid-crystal cells 116 and 128 may be substantially identical to each other, but they are generally rotated (e.g. about 180°) with respect to each other, to give less optical variation for different viewing angles. That is, the alignment directions of the liquid-crystal cells 116 and 128 may be oriented asymmetrically with respect to one another. Positioning two such liquid-crystal cells together such that the face-to-face molecule alignment directions are non-parallel may advantageously result in a lowered angular dependency of the filtering effect. Homogeneity, particularly in the dark state, may also be enhanced by the use of polarizers that are offset by about 1 to 20 degrees, as discussed in detail in U.S. Pat. No. 7,884,888 to Magnusson. Such offset polarizers may e.g. eliminate an uneven shade of the viewing area caused by variations in cell-gap geometry, unwanted birefringence in the adhesive layers of the construction, and different viewing angles. In the design of FIG. 4, second liquid-crystal cell 120 is sandwiched between polarization filters 118 and 122 that are oriented parallel to each other. Liquid-crystal cell 120 may thus be a power-lightening cell that automatically darkens if no voltage is applied. (It will be appreciated that even in the absence of an optional functionality in which a shutter darkens automatically e.g. in the event of a power interruption, the shutter will constantly provide UV and IR protection due to the presence of passive (unchanging) UV and IR blocking layers as described earlier herein.)

It will be appreciated that the designs of FIGS. 3 and 4 are merely exemplary designs and the arrangements and methods disclosed herein can be used in any automatic darkening filter, relying on any desired combination of e.g. liquid-crystal cells, polarization filters (in any orientation), band-pass filters, cover sheets, and so on.

Figure 5:
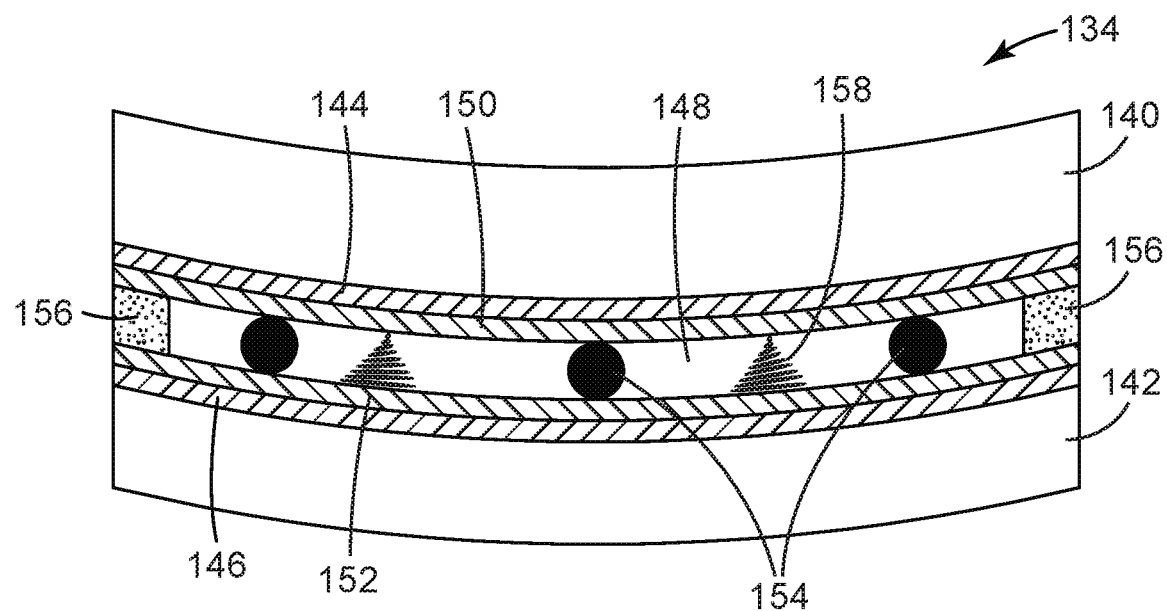
FIG. 5 is a schematic cross-sectional view of an exemplary curved liquid-crystal cell.

FIG. 5 shows an exemplary liquid-crystal cell 134 such as may be used for any of the above-described cells 116, 120, and 128. Cell 134 is a laminar construction comprising two optically-transparent flexible layers 140 and 142. Such a liquid-crystal cell can be implemented using a variety of such layers, made of e.g. glass or of any suitable organic polymeric film. The thickness of each of the layers may be about 10 micrometers (μm) to 200 μm, more typically about 30 to 150 μm, and still more typically about 75 to 125 μm. The layers 140, 142 (as present in the liquid-crystal cell) typically have a radius of less than infinite curvature, typically about 5 to 30 centimeters (cm), more typically about 7 to 20 cm. The curvature may exhibit a non-constant radius, for example, it may be parabolic, catenary, epicycloidal, and free form. Thus, for example, a curved automatic darkening filter 60 that includes shutters comprised of such liquid-crystal cells, may e.g. comprise an arcuate front-central area (directly in front of the user's eyes) with a relatively small radius of curvature and may comprise right and left side areas that are less sharply curved (e.g. are relatively planer).

On the inwardly facing surfaces of the optically-transparent flexible layers 140 and 142 are provided transparent conductive electrode layers 144 and 146, respectively, (e.g., indium tin oxide layers). By applying a voltage to the electrodes 144 and 146, an electric field is created across the liquid-crystal layer 148 to change the orientation of the liquid-crystal molecules. Juxtaposed against the electrodes 144 and 146 are alignment layers 150 and 152, respectively, for instance, a polyimide layer that has been treated mechanically, such as by brushing or rubbing, in specific alignment directions. The alignment layers 150 and 152 are spaced apart using equally sized spacers 154 inside the cells to form and maintain a gap. The cell edges can be sealed using an edge adhesive 156, such as Norland 68, available from Norland Products, Cranbury, N.J. Before the cell is completely sealed, the nematic molecules 158 are disposed within the gap between the layers 150 and 152 to form liquid-crystal layer 148. The alignment layers 150 and 152 force the liquid-crystal nematic molecules 158 to take specific angular positions at the surfaces so that the molecules are twisted through their respective twist angle between these surfaces, until being subjected to an electric field to disrupt this arrangement.

In some embodiments a twisted, nematic, liquid-crystal cell may have a twist angle of less than 100 degrees, e.g. zero or 1 to 99 degrees. In particular embodiments, such a liquid-crystal cell may have a twist angle of 1 to 85 degrees. More specifically, the twist angle of a low-twist, liquid-crystal, cell may be about 30 to 70 degrees. An automatic darkening filter that has low-twist, liquid-crystal, cells is described in U.S. Pat. No. 6,097,451 to Palmer et al.; see also U.S. Pat. No. 5,825,441 to Hornell et al. In some embodiments, a twisted, nematic liquid-crystal cell may have a higher twist angle, e.g. of about 120 degrees or more. In various embodiments, such a cell may have a twist angle of up to about 240 degrees.

Automatic darkening filter 60 as disclosed herein comprises an array of (individually) switchable shutters 10, as indicated in generic representation in FIGS. 1 and 2. It will be appreciated that the above descriptions of a switchable shutter 10 and of various components thereof (liquid-crystal cells, polarization filters, and so on), apply regardless of whether a shutter 10 is in the form of a single, large shutter that occupies the entirety of the optically active area of an automatic darkening filter, or whether it is one shutter of an array of individually switchable shutters present in the optically active area of an automatic darkening filter. It will be further appreciated that it may be possible to provide an automatic darkening filter comprising an array of individually switchable shutters in which all of the above-described components are provided separately for each shutter of the array. However, significant advantages can accrue if at least some components are shared between multiple shutters of an array of shutters.

Figure 6:
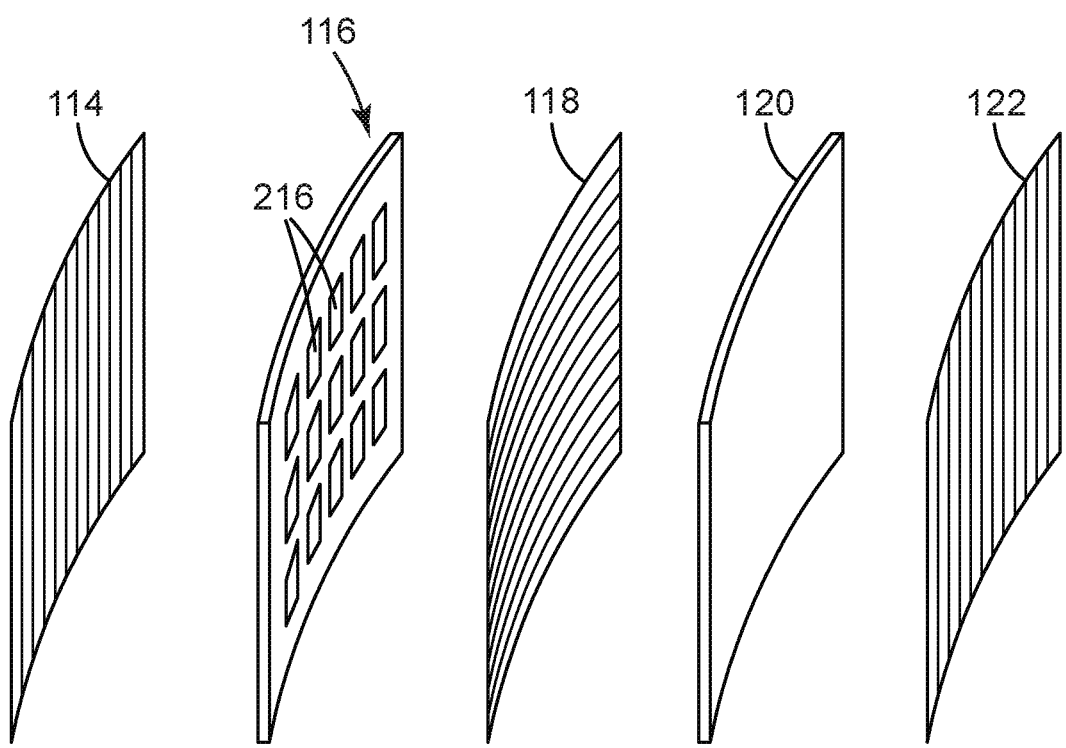
FIG. 6 is an exploded isolated side perspective view of a portion of an exemplary array of switchable shutters, provided by an array of liquid-crystal pixels, of a curved automatic darkening filter.

One such approach is shown in exemplary embodiment in FIG. 6, which relies on shutters of the general type depicted in FIG. 3 (that is, with two liquid-crystal cells interspersed among three polarizing filters in series), although the design of FIG. 6 differs from that of FIG. 3 in that the polarization filters of the second pair of polarization filters are oriented substantially orthogonally to each other). In an arrangement of the general type shown in FIG. 6, provisions are made to provide an array of individually switchable shutters. In such an approach, an array of individually switchable shutters 10 can be achieved by providing an array of liquid-crystal "pixels" 216 within first liquid-crystal cell 166, i.e. in between polarization filters 114 and 118. In such an approach, polarization filters 114 and 118, as well as third polarization filter 122, can take their usual form of extending over the length and breadth of the optically active area of automatic darkening filter 60. That is, an array of shutters may be achieved by providing an array of liquid-crystal pixels 216 of a liquid-crystal cell 116 rather than having to provide an array comprising individual liquid-crystal cells. In fact, with reference to the exemplary liquid-crystal cell design shown in FIG. 5, optically-transparent flexible layers (e.g. glass layers) 140 and 142, alignment layers 150 and 152, and even liquid-crystal layer 148, can all extend over e.g. most or all of the entire optically active area of the automatic darkening filter.

In other words, the effects disclosed herein do not necessitate that individual liquid-crystal cells 116 must be provided in discrete form (e.g. comprised of separate pairs of flexible layers 140/142, and so on) in order to obtain an array of individually switchable shutters. Rather, the providing of an array of individually switchable shutters may be achieved, for example, by configuring either or both of electrode layers 144 and 146 of a liquid-crystal cell in a desired, predetermined pattern. That is, the pattern in which a transparent conductor such as e.g. indium tin oxide is coated, e.g. in row traces and column traces, onto the surface of layers 140 and/or 142, may be controlled to allow individual areas of liquid-crystal layer 148 to be individually subjected to a control voltage. This allows particular areas (i.e., "pixels") of a liquid-crystal layer to be operated independently of other pixels of the liquid-crystal layer, such that each pixel of the liquid-crystal layer provides a separately-controllable shutter of the automatic darkening filter. Such arrangements allow some areas (shutters) of the automatic darkening filter to be e.g. switched to a dark state while allowing other areas (other shutters) to e.g. remain in a light state, with all such areas sharing the use of one or more optically-transparent flexible layers, alignment layers, and/or liquid-crystal layers.

In some embodiments, the above-described functionality may be achieved e.g. by providing pixels only within one liquid-crystal cell (layer) of the multiple liquid-crystal cells that may be present in series in the automatic darkening filter. That is, with reference to the arrangement of FIG. 6, in some embodiments a second liquid-crystal cell 120 may be a conventional (nonpixelized) liquid-crystal cell. In such cases, the changes in light/dark state that are achieved by the individual pixels 216 of first liquid-crystal cell layer 116, may be additively or subtractively superimposed on changes in light/dark state that are applied to the entire optically active area of the automatic darkening filter by second liquid-crystal cell layer 120. In other embodiments, a second liquid crystal cell 120 may be similarly provided with pixels (e.g. by manipulation of the conductive pathways as discussed above) in like manner as described for first liquid crystal cell 116. In some embodiments, such pixels of a second liquid-crystal cell 120 may be aligned and registered with the pixels 216 of the first liquid-crystal cell 116. In such arrangements, each pair of pixels of the first and second liquid-crystal cells may lie in series along an optical path through the automatic darkening filter, so that each pair of two pixels can be operated to cooperatively function as an individually controllable shutter of the automatic darkening filter.

It will be appreciated that the arrangements described herein can provide for ease of manufacturing of e.g. a curved automatic darkening filter that comprises individually switchable power-darkening shutters.

By an array of switchable shutters is meant a set of at least ten shutters (derived from a set of at least ten individually controllable liquid crystal pixels) that are arranged along at least a portion of a lateral and vertical extent of an optically active area of an automatic darkening filter (as opposed to shutters that are e.g. serially arranged along a light path). In various embodiments, an array of switchable shutters may comprise at least about 20, 40, 60, 100, 200, 400, 800, or 1600 switchable shutters. In further embodiments, an array of switchable shutters may comprise at most about 5000, 4000, 3000, 2000, 1000, 500, 300, or 150 switchable shutters.

An array of shutters 10 may have any suitable design, both in terms of the size and shape of the individual shutters, and in terms of their arrangement in an array. (It will be appreciated that the arrangement shown e.g. in FIG. 6 is a generic representation and such parameters as center-to-center spacing, edge-to-edge spacing, size and shape, as shown therein, are not to scale and are non-limiting.) In various embodiments, the individual shutters may each occupy at least about 0.1, 0.2, 0.5, 1.0, 2.0, 4.0, or 10.0 square millimeters of the automatic darkening filter. In further embodiments, the individual shutters may each occupy at most about 200, 100, 60, 40, 20, 10, or 5 square millimeters. The individual shutters may have any desired shape, e.g. at least generally rectangular (e.g. square), round, oval, or irregular. The shutters may be arranged into an array of any suitable geometric configuration (e.g., square, rectangular, hexagonal) and center-to-center spacing. The edge-to-edge spacing of the shutters may also be manipulated; e.g. it may be made as small as possible to minimize any light leakage between the individual shutters of the array. The array of shutters may occupy any desired extent of the optically active area of the automatic darkening filter. The patterning of transparent conductive layers 144 and 146 (e.g. into intersecting row traces and column traces) to provide pixels of one or more liquid-crystal cells to thus provide individual shutters of the array, may take any suitable form. In various embodiments, the patterning may be in accordance with passive-matrix or active-matrix methodologies that may be used to address and control arrays of liquid-crystal cells.

While the design and functioning of an automatic darkening filter comprising an array of switchable shutters has been described so far with reference to constructions of the general type depicted in FIG. 3, it will be appreciated that such approaches may find use in any suitable automatic darkening filter, e.g. of the general design shown in FIG. 4. For example, either or both of liquid-crystal cell (layers) 116 and 128 as depicted in FIG. 4 may include an array of liquid-crystal pixels of the general type described with reference to FIG. 6. In some embodiments, only one such liquid-crystal cell layer may bear such an array; in other embodiments, at least two such liquid-crystal layers may bear such an array. For example, in some embodiments two liquid-crystal cell layers (e.g. layers 116 and 128 of FIG. 4) may each bear an array of liquid-crystal pixels. As noted earlier, in some embodiments two such liquid-crystal layers can be oriented asymmetrically (e.g., at an angle) with respect to each other e.g. to reduce any angular dependency of the filtering effect. In such a case, the two liquid-crystal layers may each include an array of pixels; with, if desired, some or all of the liquid-crystal pixels of one array being oriented asymmetrically with regard to at least some of the liquid-crystal pixels of the other array.

Figure 7:
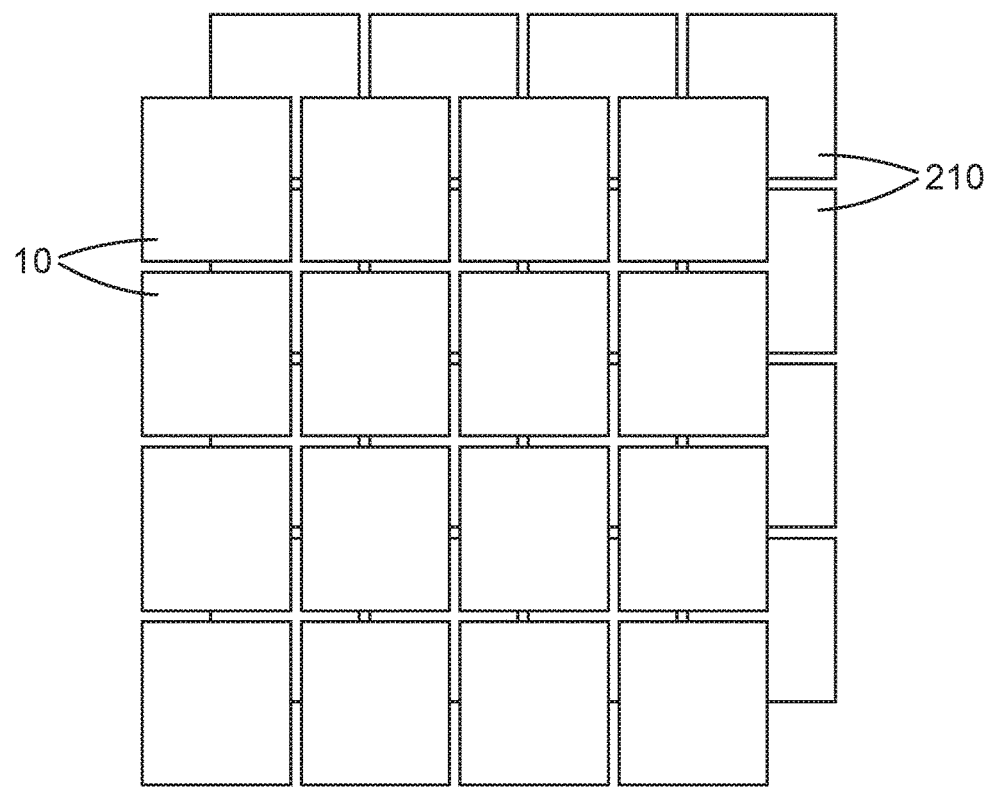
FIG. 7 is a perspective view of an exemplary arrangement of first and second arrays of switchable shutters of a curved automatic darkening filter.

In some embodiments, the presence of first and second arrays of liquid-crystal pixels (and resulting arrays of shutters) in first and second layers along an optical path of the automatic darkening filter, can be used to additional advantage. For example, at least some liquid-crystal pixels, and the resulting shutters 10, of a first array can be translationally offset in relation to at least some liquid-crystal pixels and resulting shutters 210 of a second array. Such an arrangement, which is shown in idealized representation (with any curvature not shown) in FIG. 7 with other components omitted for ease of presentation, can cause that at least some portion of any spaces that may be present between edges of individual shutters of one array, may be at least partially overlapped by shutters of the other array. This may reduce the amount of light that might be able to leak through the array of shutters of the automatic darkening filter by passing between edges of individual shutters. Any such translationally-offset arrays of shutters may be used as desired. It will be appreciated, of course, that there are other ways to compensate for such leakage, e.g. by including in the optical stack a layer with a pattern of (e.g. passive) light-blocking material that is arranged to coincide with any leakage pathways that would otherwise be present in array of shutters. Any such arrangement may be used in combination with an array (or array stack) as disclosed herein.

Automatic darkening filter 60, and switchable shutters 10 thereof, may be curved about one, two, or three axes. Typically an automatic darkening filter used in a welding helmet would be curved about one or two axes, e.g. about a vertical axis. At the very least, an automatic darkening filter will be curved (arcuate) along at least a portion of its lateral extent (i.e., curved with respect to a vertical axis) when viewed in a top view (e.g. as in the exemplary arrangement of FIG. 9). In various embodiments, the automatic darkening filter may exhibit readily identifiable curvature (e.g. corresponding to a radius of curvature of less than about 20 cm) along at least 20, 40, 80, or essentially 100% of its lateral extent when viewed in top view. The physical properties of the optically-transparent flexible layers (140 and 142) may allow for curved automatic darkening filters to be manufactured which have a radius of curvature of e.g. about 5 cm to 20 cm, and a optically active viewing area of about 10 to 600 square centimeters (cm$^2$), more typically 30 cm$^2$ to 250 cm$^2$. (Conventional welding helmets typically have an automatic darkening filter with an optically active area of about 50 to 100 cm$^2$.) The present invention may enable automatic darkening filters having a viewing area of at least 100 cm$^2$ to 125 cm$^2$ to be provided. The use of curved switchable shutters in protective headgear is discussed in detail in U.S. Patent Application Publication 2014/0013479 to Magnusson, which is incorporated by reference in its entirety herein.

As discussed in detail above, automatic darkening filter 60 will include an array of switchable shutters 10 that are each capable of controllably blocking electromagnetic radiation. That is, each individual shutter 10 can switch between at least a light state (in which is it relatively highly light-transmissive) and a dark state (in which it is relatively non-transmissive to light). In some embodiments, a shutter 10 can also switch into at least one intermediate state that exhibits a light transmissivity in between that of the light state and the dark state. In specific embodiments, a shutter 10 can switch into any of a multiplicity of intermediate states between the light state and the dark state. (Here and elsewhere herein, by "state" is meant a condition of relative light-transmissivity, or opacity, of a shutter 10 of automatic darkening filter 60.)

The amount of incident light transmitted by a shutters 10 in the various states can be characterized in various ways. One way commonly used in the art is the visible light transmission of the shutter. In various embodiments, a shutter 10 is configured so as to exhibit a visible light transmission of less than about 0.5%, less than about 0.1%, or less than about 0.05%, when in a dark state; and, to exhibit a visible light transmission of greater than about 3%, greater than about 10%, greater than about 20%, or greater than about 50%, when in a light state. In various embodiments the visible light transmission of a shutter 10 when in an intermediate state may be less than about 10%, less than about 5%, or less than about 2%, and may be greater than about 0.5%, greater than about 1%, or greater than about 1.5%. Other ranges are possible.

Performance of a shutter 10 may also be characterized by a Shade Number which is also commonly known in the art. Thus, in various embodiments a shutter 10 may exhibit a Shade Number of e.g. about 9, 10, 11, 12, 13, 14, or 15 when in a dark state. In specific embodiments, shutter 10 may exhibit a Shade Number of at least about 14 when in a dark state. In some embodiments the Shade Number of the dark state may be a pre-determined, single shade number (e.g., a factory pre-set) of 9, 10, 11, 12, 13, 14 or 15). In other embodiments the Shade Number of the dark state may be set as desired by the user (e.g., to a value of 9, 10, 11, 12, 13, 14 or 15).

In some embodiments a shutter 10 may exhibit a Shade Number of less than about 5, less than about 4, or less than about 3, when in a light state. That is, in such embodiments a "light" state e.g. to which a shutter may transition in the absence of any high intensity light being detected, may not necessarily be a completely optically transparent (unshaded) state; rather, it may be a state that corresponds to a shade number of e.g. 3 or 4. In optional embodiments in which the automatic darkening filter is configured to go to a "light" state e.g. in the event of a power interruption, such a state may be any of the above states; or, it may correspond to a shade number of 5, 6 or 7. As noted above, in some embodiments shutter 10 may be able to be set (e.g. automatically by shutter control system 16 rather than manually by a user) to an intermediate state that is between a light state and a (fully) dark state. In various embodiments, the Shade Number of shutter 10 when in an intermediate state may be e.g. 6, 7, 8, 9, 10, 11 or 12.

Figure 8:
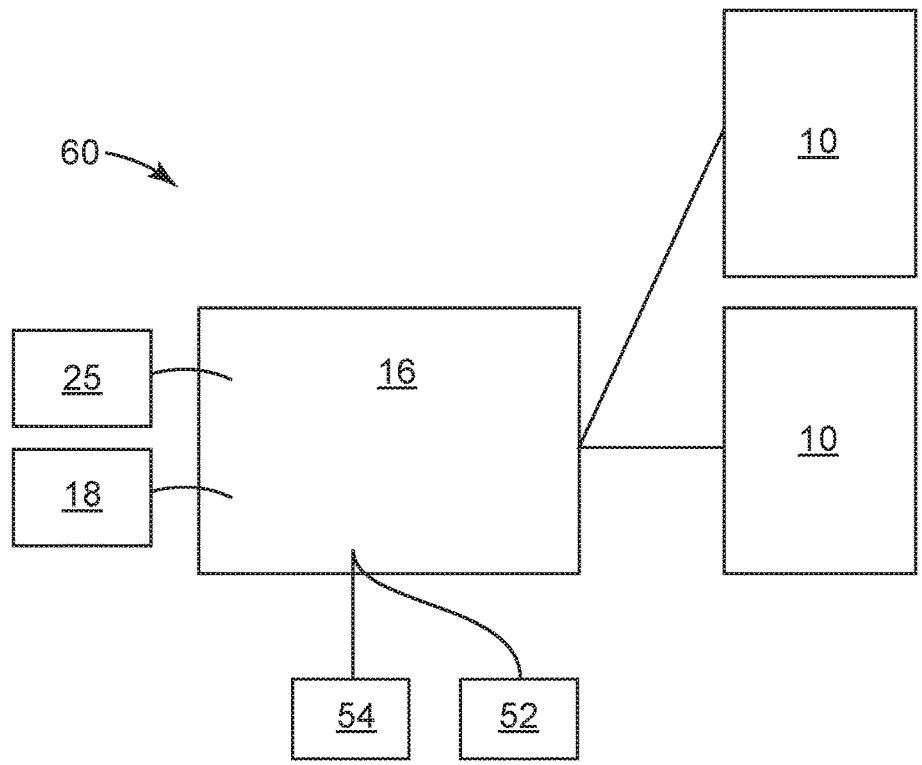
FIG. 8 is a block diagram of one embodiment of an automatic darkening filter.

With reference to the block diagram of FIG. 8, automatic darkening filter 60 comprises a shutter control system 16 that is controllably connected to the individual shutters 10 of the array of switchable shutters (only two such shutters are depicted in the generic representation of FIG. 8; in reality at least ten independently controllable shutters will be present). By controllably connected is meant that shutter control system 16 can at least send control signals to individual shutters 10 (i.e., by sending control signals to individual pixels of an array of pixels of a liquid-crystal cell, as discussed earlier herein) to assume any desired state (e.g., light, dark, intermediate, and so on). Two-way communication between control system 16 and shutters 10 is possible if desired; e.g. shutters 10 may be configured to send update or confirmation signals regarding the particular state of shutters at any given time. Shutter control system 16 can switch shutters 10 between various states by the use of any convenient control signal; for example, by varying voltages that are applied to shutters 10. Upon a change in a control signal being applied by shutter control system 16, a shutter may often exhibit a response time in lighter-to-darker transitions of less than one millisecond, and a response time in darker-to-lighter transitions of around a few milliseconds. When a constant value of a control signal is applied, a shutter typically exhibits a relatively constant light transmission.

Shutter control system 16 is receivably connected to at least one workview image acquisition device 25. By receivably connected is meant that control system 16 is configured to receive workview light intensity mapping information from the at least one workview image acquisition device. As shown in FIG. 1, acquisition device 25 is oriented so that it faces forward; specifically, so that it can acquire an image that at least generally corresponds to the workview that a wearer of headgear 1 observes through automatic darkening filter 60. Such a workview may encompass not only any high-intensity light emission from a workpiece being worked on, it may also include other portions of the workpiece (that are not emitting high-intensity light), and a small or large background area surrounding the workpiece. It may be preferential to locate image acquisition device 25 in close proximity to window 2, so that device 25 images an area that closely approximates the workview visible through the automatic darkening filter. It will be understood that in ordinary use of headgear 1, the image(s) that are acquired by an image acquisition device 25 are not displayed for, and thus are not visible to, the person who is wearing the headgear. That is, the arrangements and methods disclosed herein are not concerned with so-called virtual welding in which a user watches a projection of a workview on a display screen. Rather, the user will visualize the workview through automatic darkening filter 60 as mounted in window 2.

From this image of the workview, a signal is generated (either directly by workview image acquisition device 25, or by any ancillary microprocessor or the like that is connected thereto) that carries mapping information representative of the area distribution of light intensity within the workview. That is, each area of the workview that is depicted in the image carries information regarding the intensity of light in that area, with e.g. areas of higher light intensity and areas of lower light intensity being present over the length and breadth of the workview. Shutter control system 16 is configured to receive this signal from image acquisition device 25 (whether directly, or indirectly through some intermediary processor) and to use the information therein (along with eye position information, as discussed later herein) to determine an appropriate state to which to control various individual shutters 10 of the array of shutters. Image acquisition device 25 is thus in communication with other components of system 16 via one or more connections (which may be a dedicated wire, an optical fiber, a wireless connection, etc.), as needed for functioning of the system.

Image acquisition device 25 may be any suitable device (e.g., camera) that can acceptably acquire an image of the workview. For example, it might comprise one or more CMOS image sensors, charge-coupled devices (CCDs), or the like, so that e.g. a digital image may be generated without the need to perform analog-to-digital conversion. The wavelength range over which a sensor is most sensitive to light may be chosen appropriately. In many embodiments, an array (e.g., a solid-state array) of such sensors may be used in combination to serve collectively as device 25. In various embodiments, image acquisition device 25 may be configured to acquire images continuously, or intermittently. Similarly, the signals from image acquisition device 25 may be sent to control system 16 continuously (e.g. as a continuous video stream), or intermittently. If intermittent monitoring and/or signal transmission is utilized, it is preferably done at sufficiently high frequency to enable sufficiently rapid response of shutter 10.

Although the image acquired by device 25 may be e.g. a color map, in many embodiments it may be convenient that it be a greyscale image. That is, the value of each pixel of the image may carry only intensity information rather than also carrying color information. Any suitable image processing (e.g. spatial filtering, thresholding, edge enhancement, contrast enhancement, temporal filtering, and so on) may be performed if deemed useful to enhance the usefulness of the information.

In some embodiments, an image acquisition device 25 may exhibit a high dynamic range, meaning a dynamic range of 140 dB or greater. For example, such a device may be a logarithmic response CMOS (complementary metal oxide semiconductor) image acquisition device. In other embodiments, an image acquisition device 25 may exhibit a low dynamic range, meaning a dynamic range of less than 140 dB. In various embodiments, such a device may exhibit a dynamic range of less than 130, 120, 110, or 100 dB. It will be appreciated that in some cases a portion of the workview light intensity mapping information (e.g. at a particularly bright spot corresponding to the location of an intense light source) may hit a saturation limit, meaning that the light intensity at this location has risen above a threshold above which the workview image acquisition device does not respond to further increases in light intensity. As long as such a saturation threshold is above the light intensity which causes all shutters in the direct path between this light and the user's eye to be switched to the dark state, this will not affect the functioning of the apparatus. That is, in some embodiments such occurrences may be acceptable during ordinary use of the protective headgear.

In some embodiments the at least one workview image acquisition device can take the form of two devices (or more). In particular embodiments, two or more such devices may include a left image acquisition device 25, and a right image acquisition device 18, as shown in exemplary embodiment in FIG. 1. Such an arrangement can provide increased fidelity and accuracy in imaging and may provide a backup functionality in the event that one such device is e.g. momentarily obscured by debris. In particular embodiments, two such devices may be spaced laterally apart from each other a distance (e.g. at least about 1, 2, 4, 6 or 8 cm) that can take advantage of parallax so that the signal provided to the shutter control system includes depth of field information. This may, for example, allow the distance that a high intensity light source is away from the eyes of a wearer of the protective headgear to be taken into account by the shutter control system, to enhance the functioning described herein.

Shutter control system 16 is receivably connected to at least one eye position monitoring device 52. By receivably connected is meant that control system 16 is configured to receive information from eye position monitoring device 52 that allows the position of at least the pupil, and in some cases the entire eye (eyeball) of a wearer of the headgear, to be established (calculated) in three dimensional space with respect to the headgear and specifically with respect to the automatic darkening filter present in the window 2 of the headgear. As shown in FIG. 1, device 52 is oriented so that it faces rearward toward an eye of the wearer of the headgear.

In some embodiments a single eye position monitoring device (that is e.g. laterally centrally located) may be used to monitor the position of the right and left eyes of the wearer. However, in some embodiments it may be advantageous to provide a dedicated right eye position monitoring device 52 and a dedicated left eye position monitoring device 54, as shown in exemplary embodiment in FIG. 2. Such an arrangement may provide that information can be obtained not only with regard to the vertical and lateral position of each pupil with respect to the automatic darkening filter, but can also be used to map the front-rear (depth) distance of each pupil away from the automatic darkening filter. (It will be appreciated that, strictly speaking, information from each of the two monitoring devices may be used in combination to provide such information; however, such devices will be referred to for convenience as being right and left eye position monitoring devices.)

It will be appreciated that monitoring the spatial location of at least the pupil of a wearer's eyeball, in three dimensions, may be distinguished from tracking the direction in which a person is gazing. That is, in at least some embodiments an eye position monitoring device as disclosed herein is configured to perform functions that are different from those of co-called eye trackers (sometimes referred to as gaze trackers or scanpath trackers) that are sometimes used to monitor the gaze direction (e.g., so-called fixations and saccades) of a person while the person is observing a scene, shopping, reading, and so on. It will be appreciated that such gaze tracking is typically is not concerned with obtaining and monitoring the actual physical location of the pupil in three dimensions. For example, such gaze trackers typically will not monitor or report the actual distance, along a front-rear direction, of the pupil from a specific item such as an automatic darkening filter.

As will be appreciated based on the detailed discussions later herein, in some circumstances it may be advantageous to protect at least substantially all of the entire eye (eyeball) of a user from high intensity light, rather than simply preventing such light from entering the pupil of the eye along a pathway along which the eye is gazing. Accordingly, in some embodiments it may be desirable to monitor the actual position of all exposed portions of the eyeball with respect to the automatic darkening filter. It will be appreciated that monitoring the spatial location of the entire exposed surface of an eyeball in this manner is further distinguished from tracking the direction in which a person is gazing. In other words, in some embodiments an eye position monitoring device as disclosed herein may serve to map the location of all exposed portions of a user's eyeball relative to the headgear (and thus to the automatic darkening filter), and to update this information as needed due e.g. to the headgear shifting relative to the user's head. In particular, since many protective headgear such as welding helmets are frequently moved back and forth between an eye-shielding position and a non-shielding position, the eye position monitoring device must be able to perform its function each time that a headgear is moved back into a shielding position.

Any suitable device that obtains information that enables the location of at least the pupil (and in some cases all exposed portions) of a user's eye to be determined at any given time, may be suitable for use as an eye position monitor. In some embodiments, such a device can comprise a rearward-facing image acquisition device that obtains an image of the eyeball of a user. At least two such devices may be optimally used, so that (e.g. if both devices obtain images that overlap enough to include at least one location in common) parallax methods (or any other suitable method) can be used to ascertain the front-rear distance of at least the pupil of each eye relative to the automatic darkening filter. Since the automatic darkening filter will be a macroscopically large entity that moreover may be curved rather than being planar, in some embodiments the position of at least each pupil can be ascertained with respect to one, two, three, or more reference locations somewhere on the headgear or on the automatic darkening filter. (In some embodiments, the locations of the eye position monitoring devices themselves may conveniently serve as reference locations.)

In other words, images provided by such devices, in combination with the known locations of the devices relative to reference locations of the headgear, can be used by the shutter control system to map the position of at least the pupil (and in some cases all exposed portions of each eyeball) in three-dimensional space, relative to the reference locations. Since the location of all portions of the automatic darkening filter will be known relative to these reference locations, this allows the distance and orientation of all desired portions of the user's eyeballs, relative to all portions of the automatic darkening filter, to be determined and to be updated periodically. This information, in combination with the workview light intensity mapping information described previously, allows specific shutters of the array of shutters of the automatic darkening filter, to be identified as being on a direct optical path between a source of high intensity light in the workview and a pupil (or e.g. any exposed portion) of the eyeball of a user of the headgear.

From the above discussions it will be appreciated that an eye position monitoring device as disclosed here will not necessarily need to monitor the actual gaze direction of a user with exactness (or, in some cases, at all). However, in some embodiments an eye position monitoring device as used herein may include eye (gaze) tracking functionality. For example, the eye position monitoring device might include an eye-tracking camera that monitors corneal reflections from the eye of a user of the vision-protective headgear in order to monitor the direction the eye is gazing. However, it will be understood that any such gaze-direction information as provided e.g. by an eye tracker may not be sufficient to allow the functioning described herein. Rather, the actual position in three-dimensional space of at least the pupil of the eyeball relative to e.g. reference locations of the protective headgear should be obtained, so that a three-dimensional mapping of the location of all portions of the pupil (and in some cases of all exposed portions of the eyeball) relative to the various shutters of the automatic darkening filter, can be established. However, in some embodiments gaze tracking may be used as an adjunct to such arrangements.

Although optical monitoring has primarily been discussed, it will be appreciated that an eye position monitoring device as used herein may rely on any method that is capable of providing information as to the location of the user's eyes relative to the automatic darkening filter may be used—such alternative methods may use, e.g. in full or in part, echolocation, ultrasonic proximity sensing, or the like.

As indicated in the generic block diagram shown in FIG. 8, the arrangements disclosed herein allow a shutter control system 16 to receive workview light intensity mapping information from at least one workview image acquisition device 25/18 and eye position information from at least one eye position monitoring device 52/54, and to use the workview light intensity mapping information and the eye position information in combination to choose states (e.g., light, dark, or intermediate) to which various switchable shutters of an array, are individually switched. (By individually switched is meant that each shutter is controlled separately, even though multiple shutters may be switched at the same time in response to control signals.)

Figure 9:
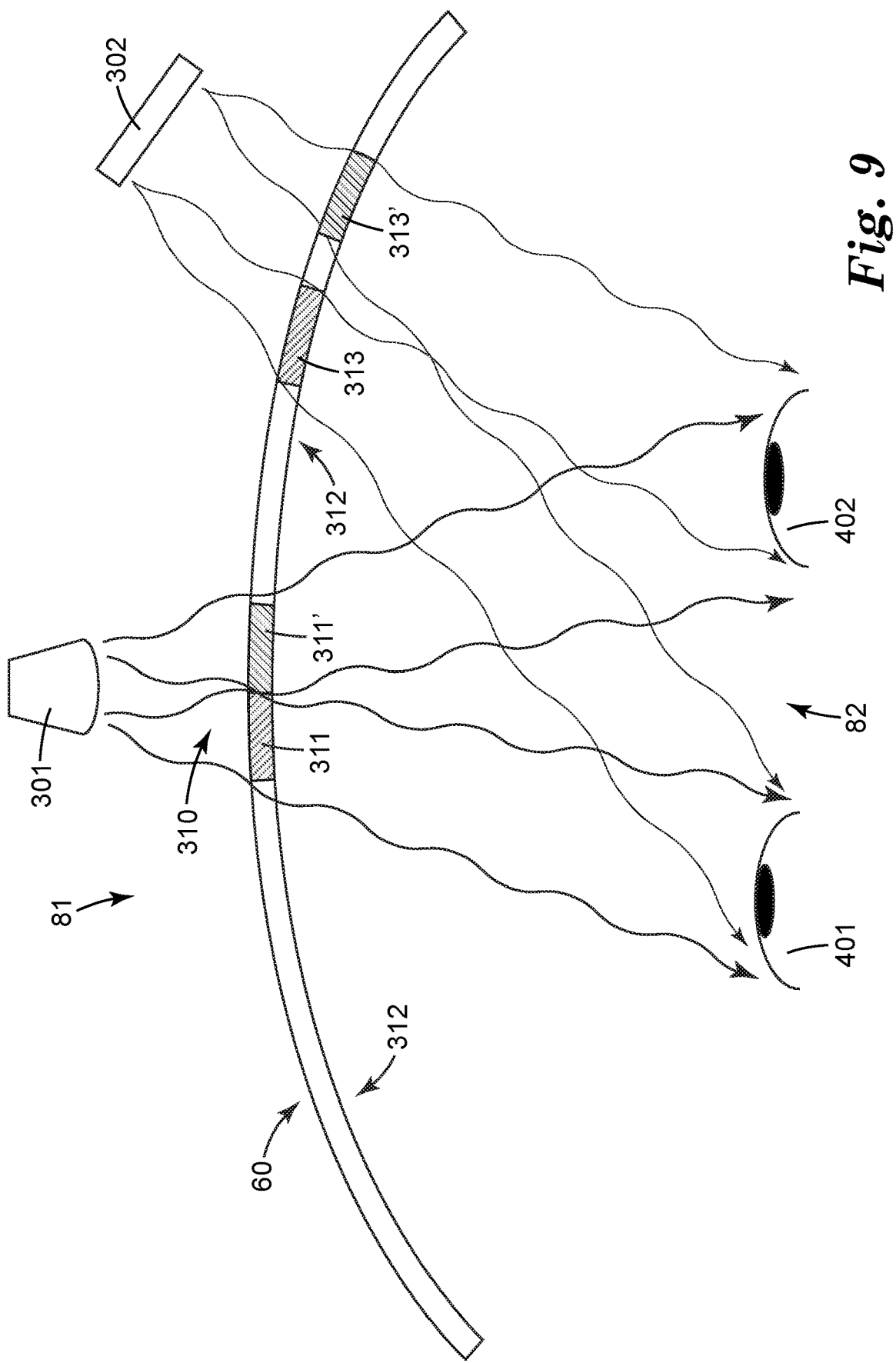
FIG. 9 is a top view in generic representation of an exemplary curved autodarkening filter comprising an array of switchable shutters, in operation in a protective headgear mounted on the head of a user.

Such functioning is discussed in further detail with reference to the generic representation of FIG. 9, which is a two-dimensional top view of a portion of an automatic darkening filter 60 mounted on the head of a user. (FIG. 9 depicts lateral (left-right) and depth (front-rear) relationships; vertical relationships are not depicted but it will be understood that such relationships are likewise taken into account in the functioning of the system.) In some embodiments, the shutter control system can use the above-described information to identify a first set 310 of switchable shutters of an array of switchable shutters as being positioned on a direct optical path between a source 301 of high intensity light in the workview and an exposed portion of an eyeball 401 of a user. In response to this information, the system can then selectively switch the first set 310 of switchable shutters from a light state to a dark state, and can then maintain first set of shutters 310 in the dark state as long as the set of shutters is on this direct optical path (e.g., as long as source 301 continues to emit high intensity light and as long as the geometric relationship of the light source, the headgear, and the person's eyeball has not changed so as to shift the location of the direct optical path). The shutter control system can also use the above-described information to identify a second set 312 of switchable shutters as not being positioned on a direct optical path between a source of high intensity light in the workview and any portion of an eyeball of the user of the headgear. The shutter control system can maintain at least some switchable shutters of the second set of switchable shutters 312 in a light state and/or it can switch at least some of these shutters to an intermediate state and maintain them in the intermediate state. This second set of shutters 312 can, but does not necessarily have to, include all of the other shutters of the array (that are not part of first set of shutters 310), as will be appreciated from discussions to follow.

While described above in regard to embodiments in which it is desired to monitor all exposed surfaces of the user's eyeball and to operate the switchable shutters in consequence of this information, it will be understood that in some embodiments the pupil of the eyeballs may be the entity that is monitored and that is used to operate the switchable shutters. In many embodiments, the shutter control system may identify a left-eye subset 311 of shutter set 310, whose shutters are on a direct optical path from a high intensity light source 301 to a left eye 401 of the user, as shown in exemplary embodiment in FIG. 9. It may also identify a right-eye subset 311' of set 310, whose shutters are on a direct optical path from a high intensity light source 301 to a right eye 402, also as shown in exemplary embodiment in FIG. 9.

It is emphasized that a set, or subset, of darkened shutters does not have to be contiguous—that is, it can be comprised of multiple discrete groups of shutters which groups do not overlap or contact each other. Thus for example, FIG. 9 shows an exemplary scenario in which a surface 302 that is sufficiently light-reflective (e.g. a polished metal surface) is oriented so as to reflect light that is emitted from source 301, toward a user's eyes, with this reflected light being high-intensity light (that is, being above the intensity threshold that requires the light to be blocked). In such a case, the set of shutters 311 that is controlled by shutter control system 16 to a dark state, may include another two subsets—left-eye subset 313 and right-eye subset 313'. Thus in this representative example, the set of darkened shutters 310 includes subsets 311, 311', 313 and 313', which subsets are not all contiguous with each other.

It will be appreciated that any real-life situation (e.g., welding operation) may include multiple direct sources of high intensity light (e.g., other welding operations may be visible in the background of the workview) and/or may include multiple sources of high intensity reflected light. (Thus, a light source as disclosed herein can be a source of reflected light and is not required to actually generate the light itself.) Accordingly, shutter control system 16 may, at various times, darken sets and/or subsets of shutters in various areas of the automatic darkening filter, as needed. It will be appreciated based on these considerations that it may not be sufficient to merely provide shutters e.g. in a laterally (and/or vertically) central area of the automatic darkening filter, since the system may occasionally be called on to deal with e.g. secondary light reflections that come in from a side angle rather than from directly ahead. Accordingly, in some embodiments the array of shutters 10 may occupy at least about 60, 70, 80, 90, 95, or substantially 100% of the optically active area of the automatic darkening filter.

As shutters of set 310 are switched to a dark state and maintained in that dark state, shutters of second set 312 may not be (at that time) on a direct optical path between any portion of an eyeball of the user and high intensity light. The shutters of second set 312 can be manipulated and/or maintained in any suitable condition. For example, in some embodiments at least substantially all shutters of second set 312 may be maintained in a light state (e.g., Shade 3 or Shade 4). In alternative embodiments, all such shutters may be switched to an intermediate state and maintained in the intermediate state. In some embodiments, such choices may be made automatically by the shutter control system (depending e.g. on the total amount of light present in the environment). In some embodiments, such choices may be user-settable at least to within certain limits.

It will be appreciated that even light that enters the pupil of a user at an off-angle (e.g., from a light source in the peripheral vision of the user) rather than directly along the line of sight may have some undesirable effect. This being the case, monitoring at least the position of the pupil can ensure that shutters of the array of shutters can be appropriately darkened to prevent off-angle-high intensity light from entering the pupil. As noted previously, in some embodiments, monitoring the entire exposed surface of the eyeball can further enhance such effects. Still further, in some situations it may be desirable to protect the entire exposed surface of a user's eyeball from high intensity light by use of an array of switchable shutters. For example, some components and surfaces of the eye (e.g. the cornea and the conjunctiva) may be susceptible to undesirable effects of high intensity light such as photokeratitis and actinic conjunctivitis, and thus may benefit from the use of individually switchable shutters (rather than e.g. depending only on the protection from UV and IR that is provided by e.g. one or more passive filtering layers of the automatic darkening filter).

It will be appreciated that the arrangements and methods disclosed herein can provide that only selected portions of an automatic darkening filter are darkened to a dark state, thus e.g. allowing a person to retain improved visibility of e.g. peripheral locations in the workview (in contrast to conventional methods which darken the entire optically active area of an automatic darkening filter, as a single "pixel"). At the same time, these arrangements and methods can serve to minimize the entry of high intensity light into the pupil of the eye, and in some embodiments can protect the entire eyeball from such light. Thus, in some embodiments, in ordinary operation of the automatic darkening filter a sufficient number of shutters may be darkened to prevent high intensity light from reaching any exposed portion of the eyeball, rather than merely closing sufficient shutters to limit the amount of high intensity light that actually enters the pupil e.g. along a direct line of sight.

Since at least some portions of the conjunctiva (e.g. the palpebral conjunctiva that surrounds the eyeball) may also be somewhat susceptible to e.g. photokeratitis, in some embodiments additional shutters may be darkened, e.g. to minimize the amount of high intensity light that reaches any portion of the palpebral conjunctiva. It will thus be appreciated that in some embodiments even some shutters that are not on a direct optical path between a high intensity light source and any portion of a user's eyeball, may nevertheless be darkened to a dark state (or e.g. to an intermediate state) if desired. In some embodiments, the amount, if any, by which the size of a darkened "spot" provided by a set of darkened shutters exceeds the actual size needed to protect the pupil, or the entire eyeball, may be chosen by the shutter control system. This may depend e.g. on the intensity of the high intensity light, the overall light intensity, etc. In some embodiments, the degree to which this "spot" size may exceed the actual size needed to protect the pupil or eyeball, may be set by the user. For example, the "spot" size may be user-settable from a minimum, up to a setting in which the entire optically active area of the automatic darkening filter darkens.

Any shutters that are not (fully) darkened may be e.g. maintained in a light state, or switched to an intermediate state and maintained in the intermediate state. In some embodiments, all shutters that are not darkened may be maintained in a light state. In some embodiments, all shutters that are not darkened may be switched to an intermediate state and maintained in the intermediate state. In some embodiments, a set of shutters that closely border the shutters that are darkened, may be switched to an intermediate state, while any remaining shutters that are far away from the darkened shutters, may be maintained in a light state. Such settings may be chosen automatically by the shutter control system, or in some embodiments they may be user-settable by the user.

It will be understood that the frequency with which the workview is imaged and with which the eye position is interrogated, the frequency with which this information is supplied to the shutter control system, and the speed with which the shutter control system processes this information and operates the various shutters, will be sufficient to enable a rapid response time to changes in the geometric relationship of the source(s) of high intensity light, the user's eyes, and the automatic darkening filter. Thus for example, if a user of the headgear turns his or her head, the darkened "spot" provided by the fully darkened shutters should "travel" along the automatic darkening filter sufficiently quickly to keep at least the pupil, and in some cases all exposed portions of the eyeball, appropriately protected. (Of course, the eye position monitoring system may be configured to account for e.g. blinking and momentary eye closures and the like.) It will be appreciated that at any given moment a particular shutter may be e.g. part of a set of darkened shutters or may be part of a set of shutters that are in a light state or are in an intermediate state.

In some embodiments protective headgear 1 may include at least one light sensor to which shutter control system 16 is receivably connected. Such a light sensor may sense the total light intensity that originates from the workview during ordinary use of headgear 1, and sends a signal that is representative of this total light intensity, to shutter control system 16. Such a light sensor may, for example, serve to provide an initial indication (signal) to shutter control system 16 that e.g. welding is taking place, so that shutter control system 16 may then activate all of the systems and components described in detail earlier herein. For example, the shutter control system and associated components may transition from a passive or "sleep" mode into an activate mode.

Shutter control system 16 (and automatic darkening filter 60 in general) can comprise (in addition to any of the above-described components) various hardware, electronic, software and/or firmware components, integrated circuits, power sources, etc., as are needed to fully carry out the functioning of the shutter control system, the image acquisition device(s), the eye position monitoring device(s), and so on. It will be clear to the ordinary artisan that shutter control system 16 and automatic darkening filter 60 can comprise any electronic components or components (e.g., one or more of resistors, amplifiers, inverters, and so on) as needed for functioning. As is customary, many of these may be provided e.g. in solid state form. In any event, shutter control system is operatively connected to the shutters of the array and, to other components, by any suitable connections, which may be may be dedicated wires, optical fibers, wireless connections, etc.

In various embodiments, protective headgear 1 may take the form of e.g. a helmet, a shield, or a visor (e.g., a welding helmet, shield or visor), noting that there may not always be bright-line boundaries between protective headgear of these categories. By definition, a protective headgear as disclosed herein does not encompass eyewear such as e.g. goggles, vision-corrective eyeglasses, ordinary safety glasses, sunglasses, and the like, that do not comprise an automatic darkening filter. In particular, the protective headgear as disclosed herein is distinguished from vision-protective articles such as lenses in sunglasses or tinted vision-correction glasses, goggles, visors, and windshields of cars, whose purpose is to minimize glare e.g. from natural light sources such as sunlight (rather than to protect the entire eye from e.g. photokeratitis arising from a welding operation). It will be appreciated that many types of light-shielding apparatus (e.g. a car windshield, a visor of a motorcycle helmet, sunglasses worn by a pilot, and so on) would not include, for example, a functionality in which shutters darken fully (or even partially) in the event of a power interruption. In at least some embodiments, the herein-described array of shutters will be present in a single, continuous pane through which light reaches both eyes (as in a window or visor of e.g. a welding helmet), rather than being present in discrete left and right panes respectively devoted to the users' left and right eyes as in e.g. sunglasses.

In various embodiments, a protective headgear and automatic darkening filter as described herein can be used in connection with industrial operations, for example welding (e.g. arc welding, torch welding, acetylene welding), cutting (e.g. laser cutting, acetylene cutting), brazing, soldering and the like. They also can be used in connection with medical procedures involving high intensity light (e.g. laser surgery, hair removal, tattoo removal, light-curing of dental resins, etc.) and other uses as well.

Although primarily described herein with regard to use in an automatic darkening filter that is curved (arcuate), it will be appreciated that at least some of the arrangements and methods disclosed herein (e.g., operating a shutter control system to protect an entire eyeball, monitoring the position of at least the pupil, or the entire eyeball, in three-dimensional space relative to reference locations of a protective headgear rather than merely monitoring the direction that the eyeball is gazing, and so on), will be similarly applicable to automatic darkening filters that are planar. Thus, some such arrangements are encompassed by the disclosures herein, e.g. as noted in the List of Exemplary Embodiments.

List of Exemplary Embodiments

Embodiment 1 is a vision-protective headgear comprising: a curved automatic darkening filter mounted in a forward-facing optically transmissive window of the vision-protective headgear, the curved automatic darkening filter comprising an array of switchable shutters that are each capable of being switched between at least a dark state and a light state; and, a shutter control system that is controllably connected to each switchable shutter of the array of switchable shutters so as to be able to control the switching of each of the switchable shutters, and that is receivably connected to at least one workview image acquisition device and to at least one eye position monitoring device; wherein the shutter control system is configured to receive workview light intensity mapping information from the at least one workview image acquisition device and eye position information from the at least one eye position monitoring device, and is configured to use the workview light intensity mapping information and the eye position information in combination to choose states to which the switchable shutters are switched.

Embodiment 2 is the vision-protective headgear of embodiment 1 wherein the shutter control system is configured to use the workview light intensity mapping information and the eye position information in combination to identify a first set of switchable shutters of the array of switchable shutters as being positioned on a direct optical path between a source of high intensity light in the workview and at least a pupil of an eyeball of a user of the headgear and wherein the shutter control system is configured to selectively switch the first set of switchable shutters from a light state to a dark state and to maintain them in the dark state; and, wherein the shutter control system is further configured to use the workview light intensity mapping information and the eye position information in combination to identify a second set of switchable shutters of the array of switchable shutters as not being positioned on a direct optical path between a source of high intensity light in the workview and at least a pupil of an eyeball of the user of the headgear and wherein the shutter control system is configured to maintain at least some switchable shutters of the second set of switchable shutters in a light state and/or to switch at least some switchable shutters of the second set of switchable shutters to an intermediate state and to maintain them in the intermediate state.

Embodiment 3 is the vision-protective headgear of any of embodiments 1-2 wherein the at least one workview image acquisition device comprises a left workview image acquisition device and a right workview image acquisition device and wherein the at least one eye position monitoring device comprises a left eye position monitoring device and a right eye position monitoring device.

Embodiment 4 is the vision-protective headgear of embodiment 3, wherein the shutter control system is configured to receive workview light intensity mapping information from the left workview image acquisition device and eye position information from the left eye position monitoring device and is configured to use this information in combination to identify a left subset of the first set of switchable shutters and wherein the shutter control system is configured to selectively switch the left subset of the first set of switchable shutters from a light state to a dark state and to maintain the left subset of switchable shutters in the dark state; and, wherein the shutter control system is configured to receive workview light intensity mapping information from the right workview image acquisition device and eye position information from the right eye position monitoring device and is configured to use this information in combination to identify a right subset of the first set of switchable shutters and wherein the shutter control system is configured to selectively switch the right subset of the first set of switchable shutters from a light state to a dark state and to maintain the right subset of switchable shutters in the dark state.

Embodiment 5 is the vision-protective headgear of any of embodiments 1-4 wherein the at least one workview image acquisition device is a high dynamic range image acquisition device that exhibits a dynamic range of at least 140 dB.

Embodiment 6 is the vision-protective headgear of any of embodiments 1-4 wherein the at least one workview image acquisition device is a low dynamic range image acquisition device that exhibits a dynamic range of less than 140 dB.

Embodiment 7 is the vision-protective headgear of any of embodiments 1-6 wherein the at least one eye position monitoring device is configured to monitor the position of at least the pupil of a user's eyeball in relation to at least one reference location of the vision-protective headgear, but wherein the eye position monitoring device is not configured to perform as an eye-tracking device that monitors a direction in which the user is gazing.

Embodiment 8 is the vision-protective headgear of embodiment 7 wherein the at least one eye position monitoring device is configured to monitor the position of at least the pupil of the user's eyeball in relation to at least three reference locations of the vision-protective headgear.

Embodiment 9 is the vision-protective headgear of any of embodiments 1-6 wherein the at least one eye position monitoring device is configured to monitor the position of at least the pupil of a user's eyeball in relation to at least one reference location of the vision-protective headgear, and wherein the eye position monitoring device is further configured to perform as an eye-tracking device that monitors a direction in which the user is gazing.

Embodiment 10 is the vision-protective headgear of embodiment 9 wherein the at least one eye position monitoring device comprises an eye-tracking camera that monitors at least corneal reflections from the eye of a user of the vision-protective headgear.

Embodiment 11 is the vision-protective headgear of any of embodiments 1-10 wherein the curved automatic darkening filter comprises first and second glass substrates that are curved so that at least one location on each of the substrates exhibits a radius of curvature of 150 mm or less, and that are locally parallel to each other at least over the entirety of an optically active area of the curved automatic darkening filter.

Embodiment 12 is the vision-protective headgear of any of embodiments 1-11 wherein the array of switchable shutters comprises at least about 20, 40, 60, 100, 200, or 400 switchable shutters.

Embodiment 13 is the vision-protective headgear of any of embodiments 1-12 wherein the array of switchable shutters is located in a first layer of the curved automatic darkening filter and occupies at least a portion of an optically active area of the first layer of the automatic darkening filter; wherein at least some switchable shutters of the array of individually shutters are power-darkening shutters that switch to a dark state when electric power is supplied thereto and that maintain the dark state as long as electric power is supplied thereto, and that switch to a light state when no electric power is supplied thereto and that maintain the light state as long as no electric power is supplied thereto.

Embodiment 14 is the vision-protective headgear of embodiment 13 wherein the curved automatic darkening filter comprises a second layer comprising an optically active area that is at least coterminous with the optically active area of the first layer of the curved automatic darkening filter, and wherein a single, switchable shutter of the second layer of the curved automatic darkening filter occupies the entirety of the optically active area of the second layer of the curved automatic darkening filter; and, wherein the single, switchable shutter of the first layer of the curved automatic darkening filter is a power-lightening shutter that switches to a light state when electric power is supplied thereto and that maintains the light state as long as electric power is supplied thereto, and that switches to a dark state when no electric power is supplied thereto and that maintains the dark state as long as no electric power is supplied thereto.

Embodiment 15 is the vision-protective headgear of any of embodiments 1-14 wherein at least selected switchable shutters of the array of switchable shutters are respectively provided at least in part by liquid-crystal pixels of an array of liquid-crystal pixels of a liquid-crystal cell that is sandwiched between a first polarizing filter sheet with a polarization axis and a second polarizing filter sheet with a polarization axis that is oriented at least substantially orthogonally to the polarization axis of the first polarizing filter sheet.

Embodiment 16 is the vision-protective headgear of embodiment 15 wherein each switchable shutter of the array of individually switchable shutters comprises a second polarizing filter that is provided by an individual area of the second polarizing filter sheet, wherein the second polarizing-filter sheet is a single second polarizing filter sheet that provides all of the second polarizing filters of all of the shutters of the array of switchable shutters.

Embodiment 17 is the vision-protective headgear of any of embodiments 15-16 wherein the array of switchable shutters is located in a first layer of the curved automatic darkening filter and occupies an optically active area of the first layer of the automatic darkening filter, wherein the curved automatic darkening filter comprises a second layer comprising an optically active area that is at least coterminous with the optically active area of the first layer of the curved automatic darkening filter, and wherein a single, switchable shutter of the second layer of the curved automatic darkening filter occupies the entirety of the optically active area of the second layer of the curved automatic darkening filter; and wherein the single, switchable shutter of the second layer of the curved automatic darkening filter is a single liquid-crystal (LC) shutter comprising a single twisted-nematic liquid-crystal cell sandwiched between the second polarizing filter sheet and a third polarizing filter sheet with a polarization axis that is oriented at least substantially orthogonal to the polarization axis of the second polarizing layer.

Embodiment 18 is the vision-protective headgear of any of embodiments 1-17 comprising a first array of individually switchable shutters located in a first layer of the curved automatic darkening filter and a second array of individually switchable shutters located in a second layer of the curved automatic darkening filter, wherein at least some shutters of the second array are each aligned in at least partial overlapping configuration with a shutter of the first array.

Embodiment 19 is the vision-protective headgear of embodiment 18 wherein the second array of individually switchable shutters is positioned in offset, partially overlapping relation with the first array of individually switchable shutters.

Embodiment 20 is a method of operating a vision-protective headgear comprising a curved automatic darkening filter comprising an array of switchable shutters that are each capable of being switched to at least a dark state and a light state and comprising a shutter control device, the method comprising: using workview light intensity mapping information and eye position information in combination to identify a first set of switchable shutters of the array of switchable shutters, which first set of switchable shutters is positioned on a direct optical path between a source of high intensity light in the workview and at least a pupil of an eyeball of a user of the headgear; using the workview light intensity mapping information and eye position information in combination to identify a second set of switchable shutters of the array of switchable shutters, which second set of switchable shutters is not positioned on a direct optical path between a source of high intensity light in the workview and at least a pupil of an eyeball of the user of the headgear; and, selectively switching the first set of switchable shutters from a light state to a dark state and maintaining them in the dark state, while maintaining at least some switchable shutters of the second set of switchable shutters in a light state and/or selectively switching at least some switchable shutters of the second set of switchable shutters to an intermediate state and maintaining them in the intermediate state.

Embodiment 21 is the method of embodiment 20 wherein the method comprises selectively switching at least substantially all of the switchable shutters of the second set of switchable shutters to the intermediate state and maintaining them in the intermediate state.

Embodiment 22 is the method of embodiment 20 wherein the method comprises switching at least substantially all of the switchable shutters of the array of switchable shutters to a light state upon using the workview light intensity mapping information and eye position information in combination to determine that no switchable shutters of the array of switchable shutters are positioned on a direct optical path between a source of high intensity light in the workview and at least a pupil of an eyeball of the user of the headgear.

Embodiment 23 is the method of any of embodiments 20-22 wherein the workview light intensity mapping information is received by the shutter control system from a workview image acquisition device and wherein at least a portion of the workview light intensity mapping information is at a saturation limit at least at some time during ordinary operation of the vision-protective headgear.

Embodiment 24 is the method of embodiment 20 performed with the vision-protective headgear of any of embodiments 1-19.

It will be apparent to those skilled in the art that the specific exemplary elements, structures, features, details, configurations, etc., that are disclosed herein can be modified and/or combined in numerous embodiments. All such variations and combinations are contemplated by the inventor as being within the bounds of the conceived invention, not merely those representative designs that were chosen to serve as exemplary illustrations. Thus, the scope of the present invention should not be limited to the specific illustrative structures described herein, but rather extends at least to the structures described by the language of the claims, and the equivalents of those structures. Any of the elements that are positively recited in this specification as alternatives may be explicitly included in the claims or excluded from the claims, in any combination as desired. Any of the elements or combinations of elements that are recited in this specification in open-ended language (e.g., comprise and derivatives thereof), are considered to additionally be recited in closed-ended language (e.g., consist and derivatives thereof) and in partially closed-ended language (e.g., consist essentially, and derivatives thereof). To the extent that there is any conflict or discrepancy between this specification as written and the disclosure in any document incorporated by reference herein, this specification as written will control.

What is claimed is:

1. A vision-protective headgear comprising:
   a curved automatic darkening filter mounted in a forward-facing optically transmissive window of the vision-protective headgear, the curved automatic darkening filter comprising an array of switchable shutters that are each capable of being switched between at least a dark state and a light state; and,
   a shutter control system that is controllably connected to each switchable shutter of the array of switchable shutters so as to be able to control the switching of each of the switchable shutters, and that is receivably connected to at least one workview image acquisition device and to at least one eye position monitoring device;
      wherein the shutter control system is configured to receive workview light intensity mapping information from the at least one workview image acquisition device and eye position information from the at least one eye position monitoring device, and is configured to use the workview light intensity mapping information and the eye position information in combination to choose states to which the switchable shutters are switched.

2. The vision-protective headgear of claim 1 wherein the shutter control system is configured to use the workview light intensity mapping information and the eye position information in combination to identify a first set of switchable shutters of the array of switchable shutters as being positioned on a direct optical path between a source of high intensity light in the workview and at least a pupil of an eyeball of a user of the headgear and wherein the shutter control system is configured to selectively switch the first set of switchable shutters from a light state to a dark state and to maintain them in the dark state; and, wherein the shutter control system is further configured to use the workview light intensity mapping information and the eye position information in combination to identify a second set of switchable shutters of the array of switchable shutters as not being positioned on a direct optical path between a source of high intensity light in the workview and at least a pupil of an eyeball of the user of the headgear and wherein the shutter control system is configured to maintain at least some switchable shutters of the second set of switchable shutters in a light state and/or to switch at least some switchable shutters of the second set of switchable shutters to an intermediate state and to maintain them in the intermediate state.

3. The vision-protective headgear of claim 2 wherein the at least one workview image acquisition device comprises a left workview image acquisition device and a right workview image acquisition device and wherein the at least one eye position monitoring device comprises a left eye position monitoring device and a right eye position monitoring device.

4. The vision-protective headgear of claim 3, wherein the shutter control system is configured to receive workview light intensity mapping information from the left workview image acquisition device and eye position information from the left eye position monitoring device and is configured to use this information in combination to identify a left subset of the first set of switchable shutters and wherein the shutter control system is configured to selectively switch the left subset of the first set of switchable shutters from a light state to a dark state and to maintain the left subset of switchable shutters in the dark state;

and, wherein the shutter control system is configured to receive workview light intensity mapping information from the right workview image acquisition device and eye position information from the right eye position monitoring device and is configured to use this information in combination to identify a right subset of the first set of switchable shutters and wherein the shutter control system is configured to selectively switch the right subset of the first set of switchable shutters from a light state to a dark state and to maintain the right subset of switchable shutters in the dark state.

5. The vision-protective headgear of claim 1 wherein the at least one workview image acquisition device is a high dynamic range image acquisition device that exhibits a dynamic range of at least 140 dB.

6. The vision-protective headgear of claim 1 wherein the at least one workview image acquisition device is a low dynamic range image acquisition device that exhibits a dynamic range of less than 140 dB.

7. The vision-protective headgear of claim 1 wherein the at least one eye position monitoring device is configured to monitor the position of at least the pupil of a user's eyeball in relation to at least one reference location of the vision-protective headgear, but wherein the eye position monitoring device is not configured to perform as an eye-tracking device that monitors a direction in which the user is gazing.

8. The vision-protective headgear of claim 7 wherein the at least one eye position monitoring device is configured to monitor the position of at least the pupil of the user's eyeball in relation to at least three reference locations of the vision-protective headgear.

9. The vision-protective headgear of claim 1 wherein the at least one eye position monitoring device is configured to monitor the position of at least the pupil of a user's eyeball in relation to at least one reference location of the vision-protective headgear, and wherein the eye position monitoring device is further configured to perform as an eye-tracking device that monitors a direction in which the user is gazing.

10. The vision-protective headgear of claim 9 wherein the at least one eye position monitoring device comprises an eye-tracking camera that monitors at least corneal reflections from the eye of a user of the vision-protective headgear.

11. The vision-protective headgear of claim 1 wherein the curved automatic darkening filter comprises first and second glass substrates that are curved so that at least one location on each of the substrates exhibits a radius of curvature of 150 mm or less, and that are locally parallel to each other at least over the entirety of an optically active area of the curved automatic darkening filter.

12. The vision-protective headgear of claim 1 wherein the array of switchable shutters comprises at least about 20, 40, 60, 100, 200, or 400 switchable shutters.

13. The vision-protective headgear of claim 1 wherein the array of switchable shutters is located in a first layer of the curved automatic darkening filter and occupies at least a portion of an optically active area of the first layer of the automatic darkening filter;

wherein at least some switchable shutters of the array of individually shutters are power-darkening shutters that switch to a dark state when electric power is supplied thereto and that maintain the dark state as long as electric power is supplied thereto, and that switch to a light state when no electric power is supplied thereto and that maintain the light state as long as no electric power is supplied thereto.

14. The vision-protective headgear of claim 13 wherein the curved automatic darkening filter comprises a second layer comprising an optically active area that is at least coterminous with the optically active area of the first layer of the curved automatic darkening filter, and wherein a single, switchable shutter of the second layer of the curved automatic darkening filter occupies the entirety of the optically active area of the second layer of the curved automatic darkening filter; and, wherein the single, switchable shutter of the second layer of the curved automatic darkening filter is a power-lightening shutter that switches to a light state when electric power is supplied thereto and that maintains the light state as long as electric power is supplied thereto, and that switches to a dark state when no electric power is supplied thereto and that maintains the dark state as long as no electric power is supplied thereto.

15. The vision-protective headgear of claim 1 wherein at least selected switchable shutters of the array of switchable shutters are respectively provided at least in part by liquid-crystal pixels of an array of liquid-crystal pixels of a liquid-crystal cell that is sandwiched between a first polarizing filter sheet with a polarization axis and a second polarizing filter sheet with a polarization axis that is oriented at least substantially orthogonally to the polarization axis of the first polarizing filter sheet.

16. The vision-protective headgear of claim 15 wherein each switchable shutter of the array of individually switchable shutters comprises a second polarizing filter that is provided by an individual area of the second polarizing filter sheet, wherein the second polarizing-filter sheet is a single second polarizing filter sheet that provides all of the second polarizing filters of all of the shutters of the array of switchable shutters.

17. The vision-protective headgear of claim 15 wherein the array of switchable shutters is located in a first layer of the curved automatic darkening filter and occupies an optically active area of the first layer of the automatic darkening filter, wherein the curved automatic darkening filter comprises a second layer comprising an optically active area that is at least coterminous with the optically active area of the first layer of the curved automatic darkening filter, and wherein a single, switchable shutter of the second layer of the curved automatic darkening filter occupies the entirety of the optically active area of the second layer of the curved automatic darkening filter;
and wherein the single, switchable shutter of the second layer of the curved automatic darkening filter is a single liquid-crystal (LC) shutter comprising a single twisted-nematic liquid-crystal cell sandwiched between the second polarizing filter sheet and a third polarizing filter sheet with a polarization axis that is oriented at least substantially orthogonal to the polarization axis of the second polarizing layer.

18. The vision-protective headgear of claim 1 comprising a first array of individually switchable shutters located in a first layer of the curved automatic darkening filter and a second array of individually switchable shutters located in a second layer of the curved automatic darkening filter, wherein at least some shutters of the second array are each aligned in at least partial overlapping configuration with a shutter of the first array.

19. The vision-protective headgear of claim 18 wherein the second array of individually switchable shutters is positioned in offset, partially overlapping relation with the first array of individually switchable shutters.

20. A method of operating a vision-protective headgear comprising a curved automatic darkening filter comprising an array of switchable shutters that are each capable of being switched to at least a dark state and a light state and comprising a shutter control device, the method comprising:
using workview light intensity mapping information and eye position information in combination to identify a first set of switchable shutters of the array of switchable shutters, which first set of switchable shutters is positioned on a direct optical path between a source of high intensity light in the workview and at least a pupil of an eyeball of a user of the headgear;
using the workview light intensity mapping information and eye position information in combination to identify a second set of switchable shutters of the array of switchable shutters, which second set of switchable shutters is not positioned on a direct optical path between a source of high intensity light in the workview and at least a pupil of an eyeball of the user of the headgear; and,
selectively switching the first set of switchable shutters from a light state to a dark state and maintaining them in the dark state, while maintaining at least some switchable shutters of the second set of switchable shutters in a light state and/or selectively switching at least some switchable shutters of the second set of switchable shutters to an intermediate state and maintaining them in the intermediate state.

21. The method of claim 20 wherein the method comprises selectively switching at least substantially all of the switchable shutters of the second set of switchable shutters to the intermediate state and maintaining them in the intermediate state.

22. The method of claim 20 wherein the method comprises switching at least substantially all of the switchable shutters of the array of switchable shutters to a light state upon using the workview light intensity mapping information and eye position information in combination to determine that no switchable shutters of the array of switchable shutters are positioned on a direct optical path between a source of high intensity light in the workview and at least a pupil of an eyeball of the user of the headgear.

23. The method of claim 20 wherein the workview light intensity mapping information is received by the shutter control system from a workview image acquisition device and wherein at least a portion of the workview light intensity mapping information is at a saturation limit at least at some time during ordinary operation of the vision-protective headgear.

* * * * *

UNITED STATES PATENT AND TRADEMARK OFFICE
CERTIFICATE OF CORRECTION

PATENT NO. : 11,160,687 B2
APPLICATION NO. : 16/622607
DATED : November 2, 2021
INVENTOR(S) : Brit Billingsley et al.

It is certified that error appears in the above-identified patent and that said Letters Patent is hereby corrected as shown below:

In the Claims

Column 24
Line 41, In Claim 13, delete "individually shutters" and insert -- individually switchable shutters --, therefor.

Column 25
Line 11, In Claim 16, delete "polarizing-filter" and insert -- polarizing filter --, therefor.

Column 26
Line 12, In Claim 20, insert -- the -- before "eye position".

Signed and Sealed this
Twelfth Day of April, 2022

Drew Hirshfeld
*Performing the Functions and Duties of the
Under Secretary of Commerce for Intellectual Property and
Director of the United States Patent and Trademark Office*